(12) United States Patent  
Yamauchi et al.

(10) Patent No.: US 11,083,493 B2  
(45) Date of Patent: Aug. 10, 2021

(54) MECHANISM FOR HOLDING ELONGATE MEDICAL APPARATUS

(71) Applicant: TOHOKU UNIVERSITY, Miyagi (JP)

(72) Inventors: Daisuke Yamauchi, Miyagi (JP); Yoichi Haga, Miyagi (JP); Tetsuaki Kawase, Miyagi (JP); Yukio Katori, Miyagi (JP); Kyoichi Akiyama, Miyagi (JP); Tadao Matsunaga, Miyagi (JP)

(*) Notice: Subject to any disclaimer, the term of this patent is extended or adjusted under 35 U.S.C. 154(b) by 169 days.

(21) Appl. No.: 16/089,592

(22) PCT Filed: Mar. 31, 2017

(86) PCT No.: PCT/JP2017/013842  
§ 371 (c)(1),  
(2) Date: Sep. 28, 2018

(87) PCT Pub. No.: WO2017/171085  
PCT Pub. Date: Oct. 5, 2017

(65) Prior Publication Data  
US 2019/0117258 A1    Apr. 25, 2019

(30) Foreign Application Priority Data  
Mar. 31, 2016    (JP) .............................. JP2016-071391

(51) Int. Cl.  
*A61B 17/34*    (2006.01)  
*A61F 11/00*    (2006.01)  
(Continued)

(52) U.S. Cl.  
CPC ........ *A61B 17/3468* (2013.01); *A61B 1/0014* (2013.01); *A61B 1/227* (2013.01);  
(Continued)

(58) Field of Classification Search  
CPC ... A61B 17/3468; A61B 1/0014; A61B 1/227; A61B 17/32; A61B 17/34;  
(Continued)

(56) References Cited

U.S. PATENT DOCUMENTS 6,770,070 B1 *   8/2004  Balbierz ................ A61B 10/04  
                                                                        600/566  
2005/0234297 A1 * 10/2005  Devierre ............ A61B 1/00098  
                                                                        600/153

(Continued)

FOREIGN PATENT DOCUMENTS

GB      2 437 708       11/2007  
JP       3102563        10/2000  
(Continued)

OTHER PUBLICATIONS

International Search Report dated Jun. 27, 2017 in International (PCT) Application No. PCT/JP2017/013842.

*Primary Examiner* — Kathleen S Holwerda  
*Assistant Examiner* — Brooke Labranche  
(74) *Attorney, Agent, or Firm* — Wenderoth, Lind & Ponack, L.L.P.

(57) ABSTRACT

A cochlear implant insertion-assisting device includes a tubular member configured to hold a cochlear implant. The tubular member includes a cut extending in a longitudinal direction. The cochlear implant insertion-assisting device can selectively switch between a first state in which the cochlear implant is held and a second state in which the cochlear implant can be released.

7 Claims, 17 Drawing Sheets

(51) Int. Cl.
*A61B 1/227* (2006.01)
*A61F 2/18* (2006.01)
*A61B 1/00* (2006.01)
*A61N 1/05* (2006.01)

(52) U.S. Cl.
CPC ........... *A61F 2/18* (2013.01); *A61F 11/00* (2013.01); *A61F 11/004* (2013.01); *A61F 2002/183* (2013.01); *A61N 1/0541* (2013.01)

(58) Field of Classification Search
CPC ........... A61B 17/3209; A61B 17/3417; A61B 17/3478; A61F 11/00; A61F 11/004; A61F 2002/183; A61F 2/18; A61N 1/0541
See application file for complete search history.

(56) References Cited

U.S. PATENT DOCUMENTS

| | | | |
|---|---|---|---|
| 2008/0103357 | A1 | 5/2008 | Zeiner |
| 2008/0213897 | A1 | 9/2008 | Jamruszka-Lewis |
| 2013/0089392 | A1 | 4/2013 | Iida |
| 2016/0038014 | A1* | 2/2016 | Molnar ............ A61M 16/0456 600/109 |

FOREIGN PATENT DOCUMENTS

| | | |
|---|---|---|
| JP | 2001-506546 | 5/2001 |
| JP | 2007-215900 | 8/2007 |
| JP | 4294248 | 7/2009 |
| JP | 2010-179021 | 8/2010 |
| JP | 2011-250880 | 12/2011 |
| JP | 5383999 | 1/2014 |
| WO | 01/58381 | 8/2001 |

* cited by examiner

Fig. 10
(A)
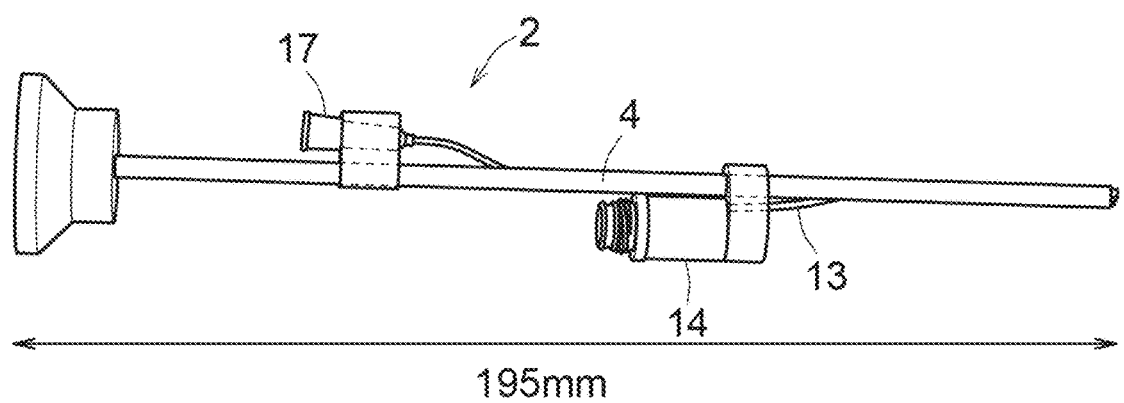
(B)
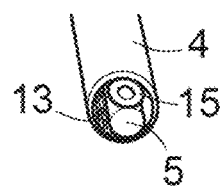

COCHLEA MODEAL

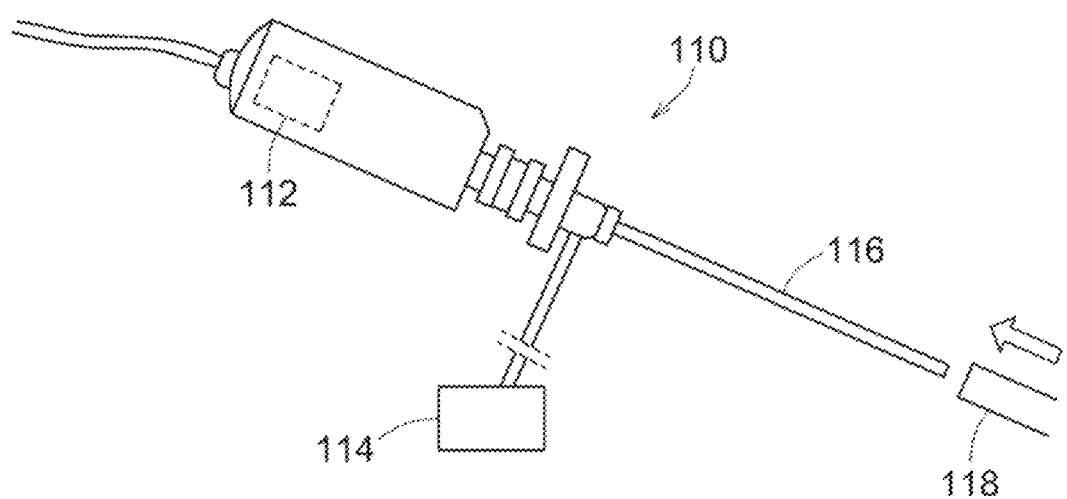

MECHANISM FOR HOLDING ELONGATE MEDICAL APPARATUS

TECHNICAL FIELD

The present invention relates to a holding mechanism for elongate medical equipment, and more particularly relates to an ear implant guiding device.

BACKGROUND ART

For patients who have become hard of hearing due to the inner ear, a technique exists for recovering hearing by embedding an electrode known as a Cochlear Implant (CI) in the cochlea. This cochlear implant surgery is increasing each year, and at present, approximately 600 cases of this surgery are annually performed in Japan. Cochlear implant surgery is not only a challenge in cases of congenital high-sensitivity hearing loss in children, but also a problem for healthy longevity in aging societies, and demand is growing on a large-scale for elderly hearing-impaired individuals. In recent years, as electrical acoustic stimulation-type cochlear implants have fallen under insurance protection, soft surgery of the inner ear is attracting attention.

CIs are composed of two components including an extra-corporeal device and an intra-corporeal device. The extra-corporeal device is a device that is mounted on the head, and is equipped with a transmission coil for transmitting received voices and sounds to a receiving coil in the intra-corporeal device. The intra-corporeal device is a device that is implanted in the body. FIG. 16 illustrates an example of the intra-corporeal device 100 of the CI, where the intra-corporeal device 100 includes a main body portion 101 provided with a receiving coil and an electrode portion 102 to be inserted into the cochlea. The material of the receiving coil is titanium, and the electrode portion 102 is covered with a silicone material so as not to damage the cochlea.

When implanting the CI intra-corporeal device 100 in the inner ear, a drill is used to scrape the bone behind the ear and the main body portion 101 is attached as illustrated in FIG. 17. Then, a hole of approximately 3 mm×6 mm is opened at the position of the wall of the retrotympanum on the rear side behind the tympanic membrane indicated by the circled numeral 104 in FIG. 17 (retrotympanotomy), an additional hole of approximately 1 mm is opened in the cochlea 105 (cochleostomy), and the tip of the electrode portion 102 of the intra-corporeal device 100 is passed through the hole of the cochlea 105 and inserted into the hole along the winding direction of the cochlea 105. In this regard, since the small-diameter elongated portion of the intra-corporeal device 100 that includes the electrode portion 102 is made of a soft material such as a silicone resin so as not to damage the cochlea 105, there is a problem in which it buckles when inserted into a narrow cochlea, such that insertion is difficult.

In addition, with respect to the inner ear, which serves as a sensor for hearing and equilibrium functions, in a case where inner ear lymph fluid leaks and a small amount of air enters, its function is easily lost. For this reason, at the time of ear surgery of the inner ear, it is necessary to fill the surgical field with a liquid in order to preserve the function of the inner ear. However, while there are uterine or urinary endoscopes provided with perfusion flow paths for blood purification (PTL 1), there are no endoscopes exclusively for ears that are equipped with perfusion functionality for filling the surgical field. Accordingly, as illustrated in FIG. 18, a tube 118 was placed on the outer circumferential surface of a sheath 116 of a known endoscope 110 used for otological surgery and provided with an imaging device 112, a light source 114, and the sheath 116 for housing a plurality of fibers and lenses, and physiological saline serving as a perfusion fluid is poured in an annular cross-section space between the sheath 116 and the tube 118. However, problems arise that the diameter of the sheath 116 becomes large (the diameter of the sheath 116 is 2.7 mm, whereas the diameter of the tube 118 is 4.0 mm), that it takes time and effort to attach and detach the tube 118 before and after surgery, and that force is applied toward the proximal portion of the sheath 116 when the tube 118 is attached to the sheath 116, which may cause failure of the endoscope 110 or the like.

Accordingly, there is demand for the development of an insertion-assisting device capable of being attached to an endoscope system and configured to hold the cochlear implant and assist stable insertion of the cochlear implant into the inner ear. This also applies to the case of elongated medical instruments other than cochlear implants, such as implants for ears and the like. It is preferable that the endoscope system includes a safe and efficient perfusion function.

CITATION LIST

Patent Literature

PTL 1: JP 2010-179021 A

SUMMARY OF INVENTION

Technical Problem

One object of the present invention is to provide a holding mechanism capable of selectively holding and releasing an elongated medical instrument.

Solution to Problem

To achieve the above object, the present inventors discovered that by attaching, to a tip portion of an endoscope sheath, a holding mechanism that has a specific structure and that is movable along the sheath, easy guidance of elongated medical instruments such as CIs can be performed, and the present invention was completed.

According to the present invention, a holding mechanism for a medical instrument having an elongated shape is provided, the holding mechanism including: a tubular member configured to hold a medical instrument. The tubular member includes a cut extending in a longitudinal direction, and the holding mechanism can selectively switch between a first state in which the medical instrument is held and a second state in which the medical instrument can be released.

In one embodiment, the tubular member includes: a first tubular member including a cut extending in a longitudinal direction, and a second tubular member including a cut extending in the longitudinal direction and disposed inside the first tubular member. Widths of the first tubular member and the second tubular member are greater than a diameter of the medical instrument; and in the second state, a position of the cut of the first tubular member and a position of the cut of the second tubular member are aligned by rotating the second tubular member, and the medical instrument held inside the second tubular member is allowed to be released.

In another embodiment, in the second state, the tubular member allows the medical instrument held inside to be released by expanding a width of the cut to be greater than an outer diameter of the medical instrument.

In another embodiment, a shape-memory alloy wire is wound around the tubular member; and in the second state, the width of the cut of the tubular member expands to be greater than an outer diameter of a medical instrument by shrinking of a shape-memory alloy wire due to electric heating, and a medical instrument is allowed to be released.

In another embodiment, a polymer tube covers a shape-memory alloy wire.

In another embodiment, the medical instrument is a cochlear implant or an artificial ear ossicle.

In another embodiment, the holding mechanism is an attachment device configured to be attached to an endoscope.

Advantageous Effects of Invention

According to the holding mechanism for a medical instrument having an elongated shape of the present invention, it is possible to stably guide or insert an elongated medical instrument, such as an ear implant, to a predetermined position. In addition, when used in conjunction with an endoscope, the surgical field of the inner ear can be filled with perfusion fluid.

BRIEF DESCRIPTION OF DRAWINGS

FIG. 7A illustrates a state in which a cochlear implant is held, FIG. 7B illustrates a state in which a cochlear implant is released, FIG. 7C is an end view of FIG. 7A, and FIG. 7D is an end view of FIG. 7B.

FIG. 10A illustrates a photograph of an underwater otological surgery endoscope of an embodiment, and FIG. 10B illustrates a tip end view of the endoscope in FIG. 10A.

FIG. 18 is a schematic diagram illustrating an example of an endoscope having a perfusion function according to the related art.

DESCRIPTION OF EMBODIMENTS

Hereinafter, an embodiment in which the present invention is implemented in an ear endoscope system provided with a cochlear implant insertion-assisting device will be described with reference to FIG. 1 to FIG. 8C.

Figure 1:
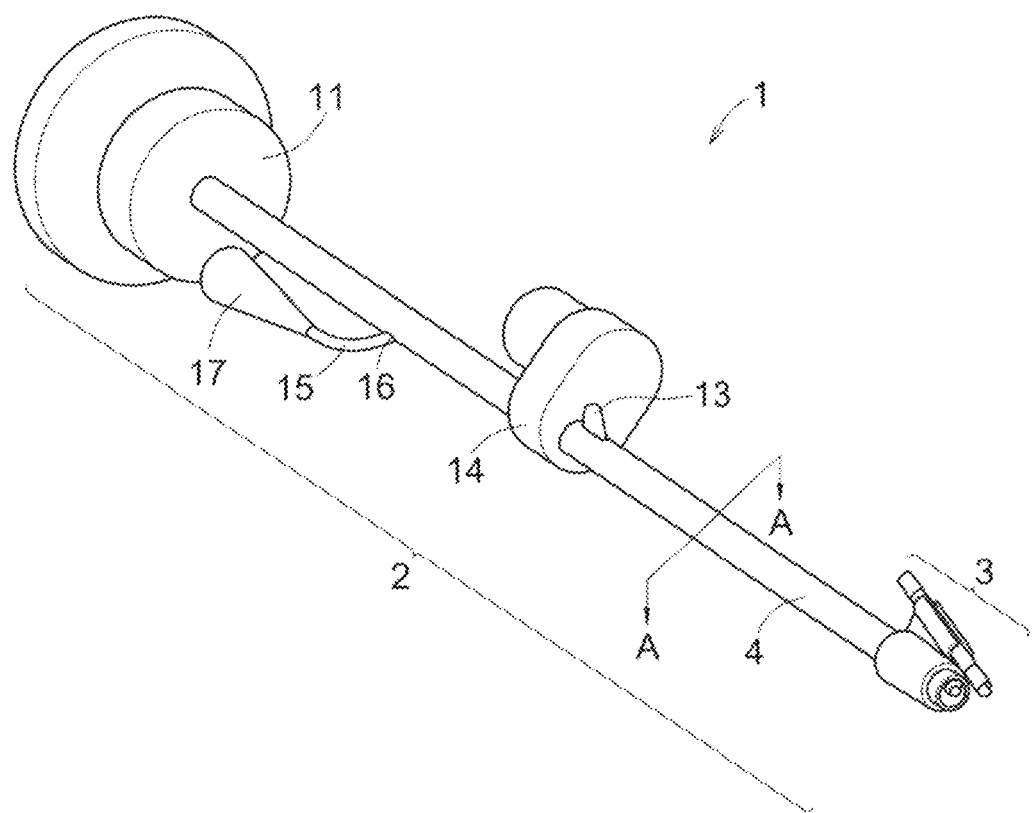
FIG. 1 is a schematic perspective view of an ear endoscope system according to a first embodiment of the present invention.

As illustrated in FIG. 1, the ear endoscope system 1 includes an endoscope 2 (only a portion of the tip side of the endoscope 2 is illustrated in FIG. 1), which is a rigid endoscope for ears, and a cochlear implant insertion-assisting device 3, which is an attachment device attached to the endoscope 2. The cochlear implant insertion-assisting device serves as a holding mechanism or a holding device for elongated medical instruments. The cochlear implant insertion-assisting device 3 is attached to the sheath 4 so as to be movable along the sheath 4 of the endoscope 2 in the longitudinal direction. The sheath 4 may be made from any material, and, for example, may be made from a stainless steel pipe.

Figure 2:
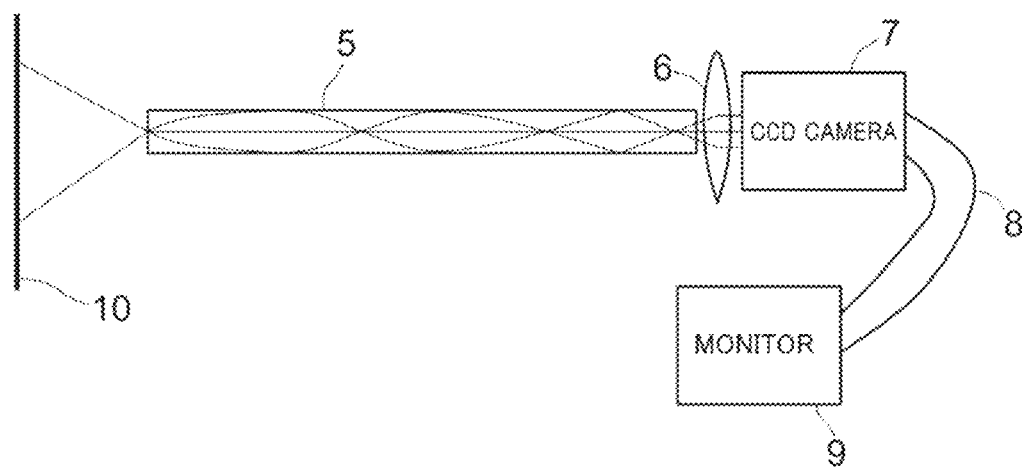
FIG. 2 is a schematic diagram of an illumination system of an endoscope.

The observation system of the endoscope 2 will be described. As illustrated in FIG. 2, an elongated rod lens 5 and an eyepiece 6 disposed on the proximal side of the rod lens 5 are provided inside the sheath 4 of the endoscope 2. The eyepiece 6 is optically connected to a CCD camera 7 via a jig 11 (see FIG. 1), and the CCD camera 7 is further connected to a monitor 9 as a display device with wiring 8 therebetween. Commercially available items for endoscopes can be used for the rod lens 5, the eyepiece 6, the CCD camera 7, and the monitor 6. With such a configuration, an image of a target object 10 is acquired and observed on the monitor 9.

Figure 3:
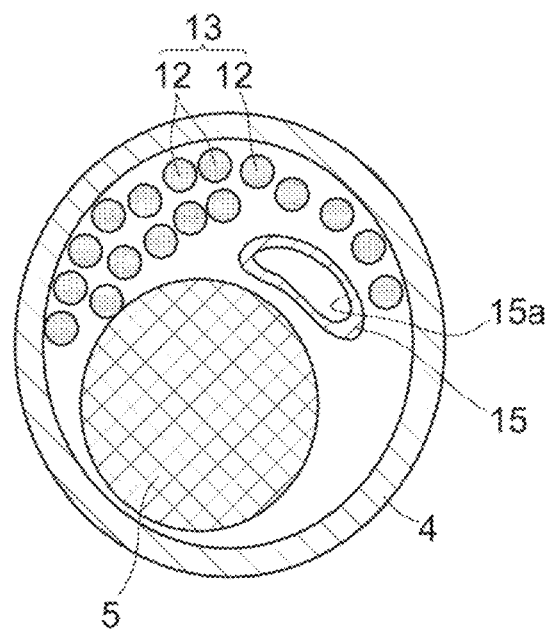
FIG. 3 is a schematic cross-sectional view taken along the line A-A of FIG. 1.

Furthermore, as illustrated in FIG. 1 and FIG. 3, as the illumination system, an optical fiber bundle 13 composed of a plurality of optical fibers 12 for guiding illumination light from a light source device to the tip of the endoscope 2 is disposed inside the endoscope 2. The optical fiber bundle 13 is connected to a light guide (not illustrated) by a jig 14.

As illustrated in FIG. 3, as a perfusion system, the ear endoscope system 1 is provided with a tube 15 for liquid perfusion inside the sheath 4 of the endoscope 2. The tube 15 is preferably a flexible tube having a lumen 15a, such as a silicone rubber tube. As illustrated in FIG. 1, the proximal portion of the liquid perfusion tube 15 extends out from the sheath 4 through a hole 16 provided in the sheath 4, and is connected to the tip of the substantially conical cap 17 at the tip of the syringe so that fluid movement is possible. Accordingly, a syringe containing a perfusion fluid such as a liquid having the composition of a body fluid (such as perilymph fluid), a physiological saline solution, or other buffer solution is connected to the cap 17. When the perfusion fluid is pushed out from the plunger of the syringe toward the tip of the cap 17, the perfusion fluid flows in the lumen 15a of the tube 15 toward the tip of the sheath 4, and the perfusion fluid can be delivered from the sheath 4 of the endoscope 12. According to this configuration, the operation site can be filled with the perfusion fluid prior to the implantation of the cochlear implant (CI) described later. According to this configuration, the outer diameter of the sheath 4 can be suppressed to smaller than 4.0 mm, such as smaller than or equal to 3.8 mm, for example.

Figure 4:
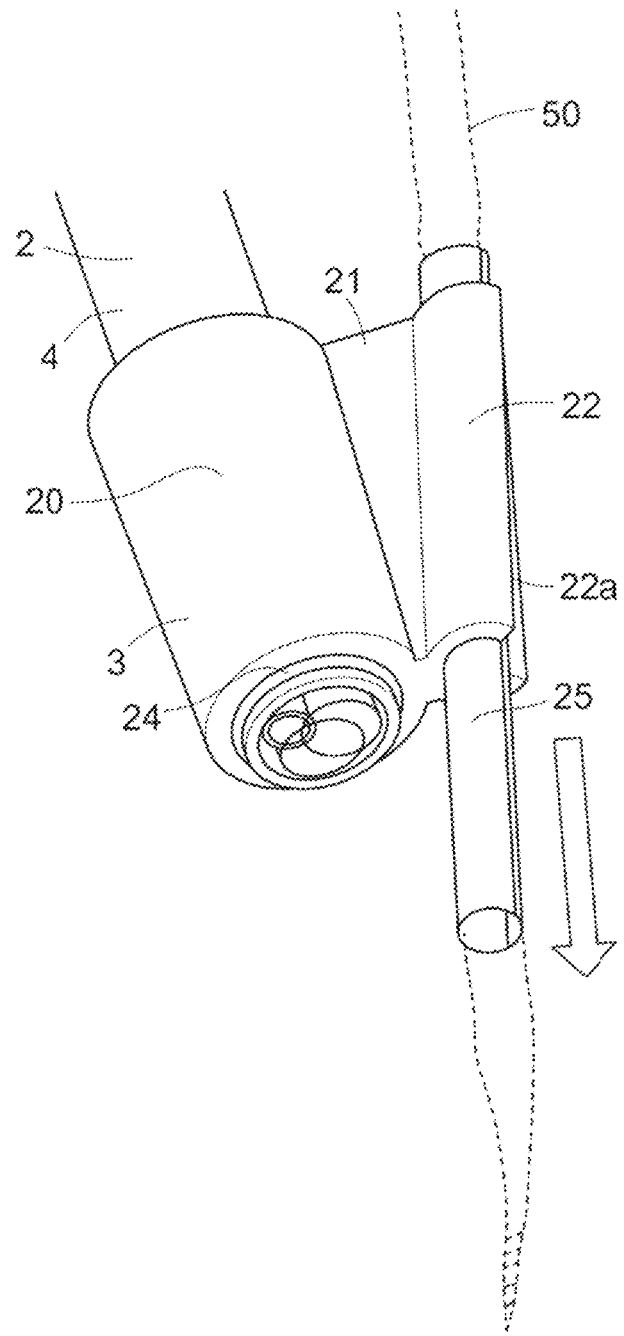
FIG. 4 is an enlarged schematic perspective view of a cochlear implant insertion-assisting device.

Next, the cochlear implant insertion-assisting device 3 will be described in detail. As illustrated in FIG. 4, the cochlear implant insertion-assisting device 3 includes a hollow, substantially cylindrical main body 20 configured to be attached around the sheath 4 of the endoscope 2, a holding portion 22 connected in parallel to the main body 20 with a connection unit 21 therebetween and configured to hold a cochlear implant (CI) 50 as an object to be held, a tubular member 24 provided in the main body 20, and a tubular member 25 that is inserted into the holding portion 22 and has a length longer than that of the holding portion 22. In this embodiment, the main body 20, the connection unit 21, and the holding portion 22 may be formed of any material such as metal or synthetic resin, but are preferably formed of a synthetic resin such as urethane resin. In the present embodiment, although the main body 20, the connection unit 21, and the holding portion 22 are formed as one unit, the main body 20, the connection unit 21, and the holding portion 22 may be formed separately and subsequently joined together. The tubular members 24 and 25 may also be formed from any material, but are preferably formed from a synthetic resin such as polyolefin or polyimide. The holding portion 22 and the tubular member 25 extend obliquely with respect to the extending direction (that is, the longitudinal direction of the sheath 4) of the main body 20. In addition, the holding portion 22 has a substantially C-shaped cross section, and includes an opening portion 22a that opens along the longitudinal direction. As will be described in detail later, by having the electrode portion 52 of the cochlear implant 50 (more precisely, the intra-corporeal device of the cochlear implant 50) pass through the holding portion 22 of the cochlear implant insertion-assisting device 3 from the proximal side and advancing the cochlear implant 50 passed through the holding portion 22 in the tip direction (the direction of the arrow), the cochlear implant 50 is guided through the path, and it becomes easy to insert a small-diameter linear portion including the electrode of the cochlear implant 50 into the cochlea. Since the cochlear implant insertion-assisting device 3 functions to guide the cochlear implant 50 to a predetermined position of the inner ear, it can also be referred to as a cochlear implant guiding device.

Figure 5:
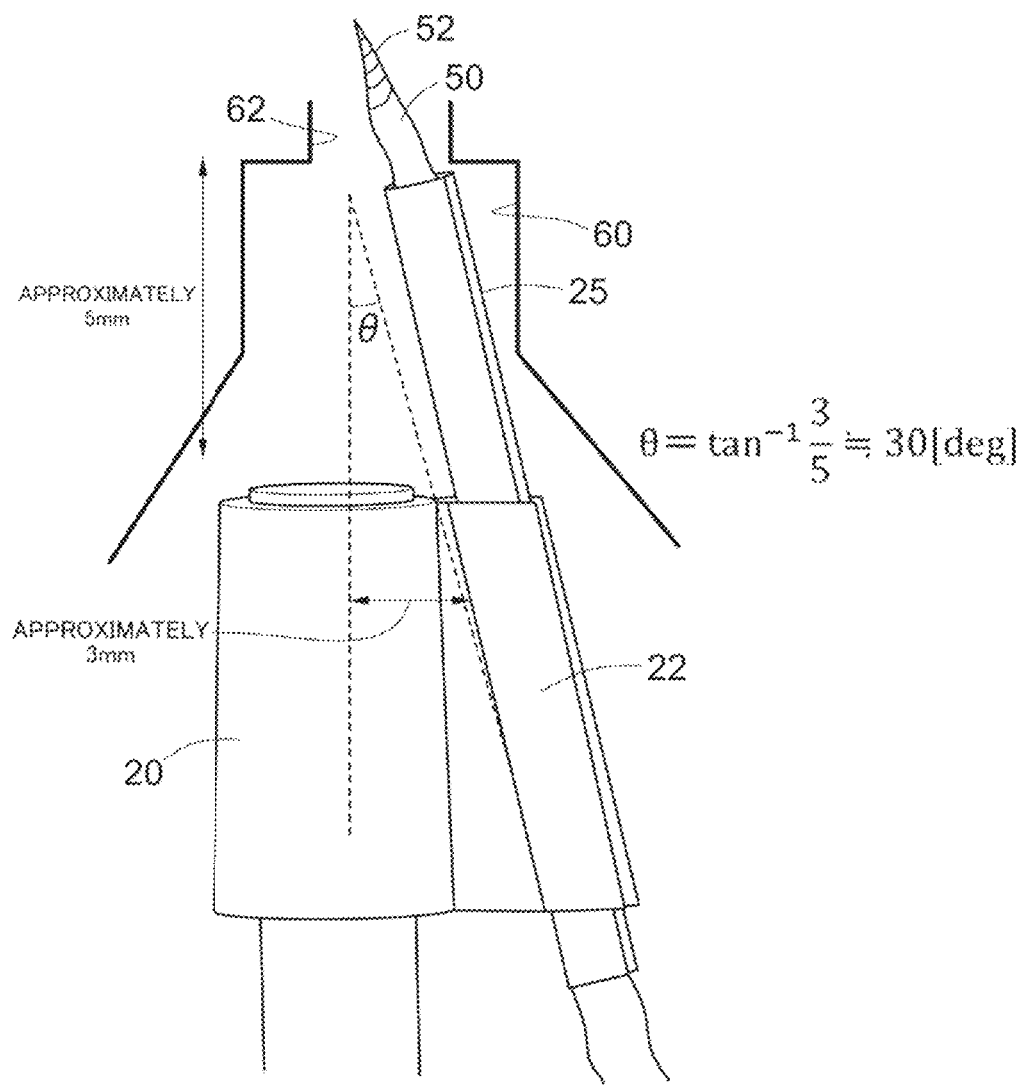
FIG. 5 is a schematic diagram for illustrating an angle θ formed by a holding portion of a cochlear implant insertion-assisting device and a direction in which a tubular member extends.
Figure 6:
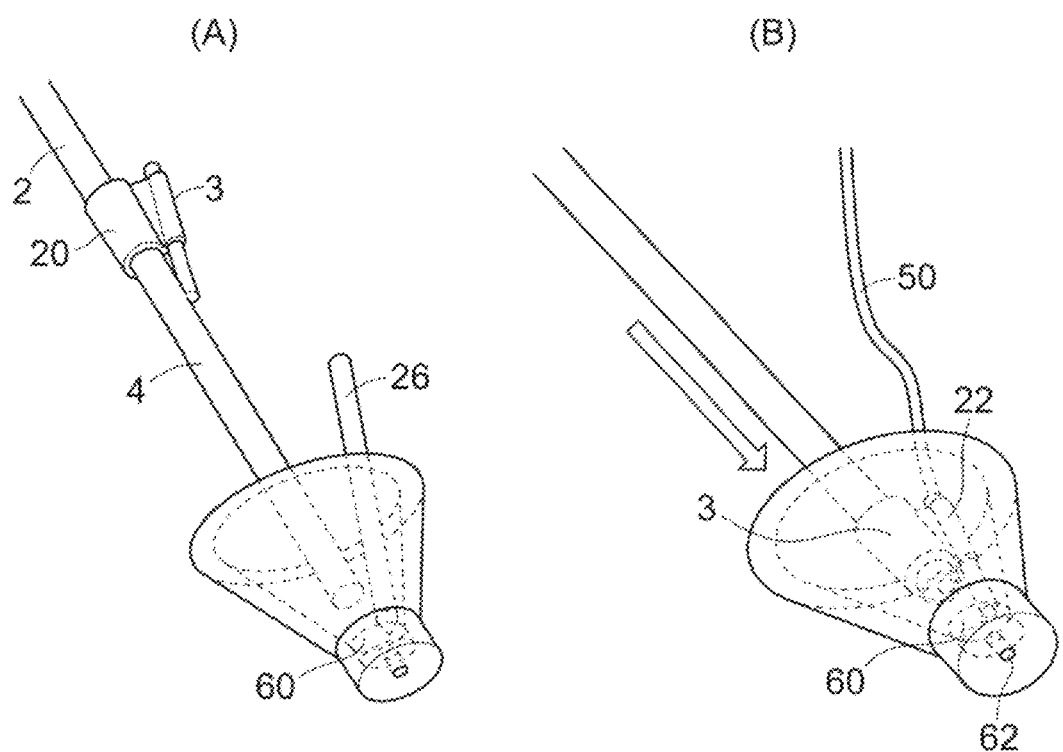
FIG. 6A and FIG. 6B are explanatory diagrams of a method of using a cochlear implant insertion-assisting device.
Figure 7:
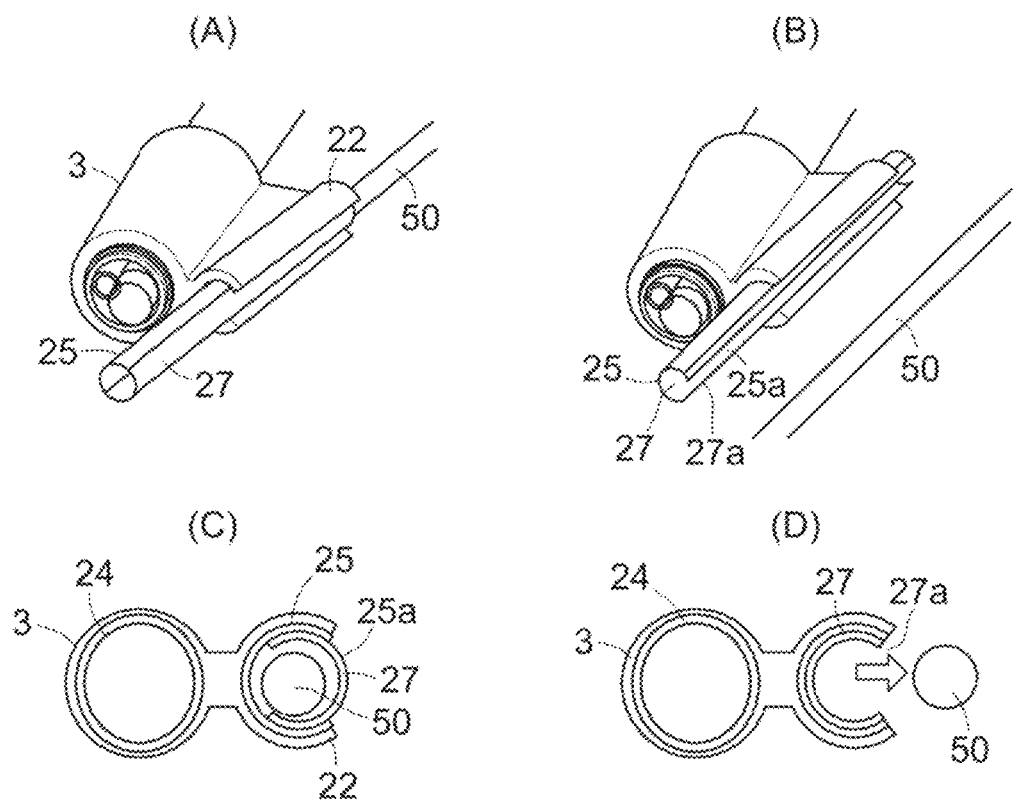
FIGS. 7A to 7D illustrate an example of a rotation-type cochlear implant release mechanism.
Figure 8:
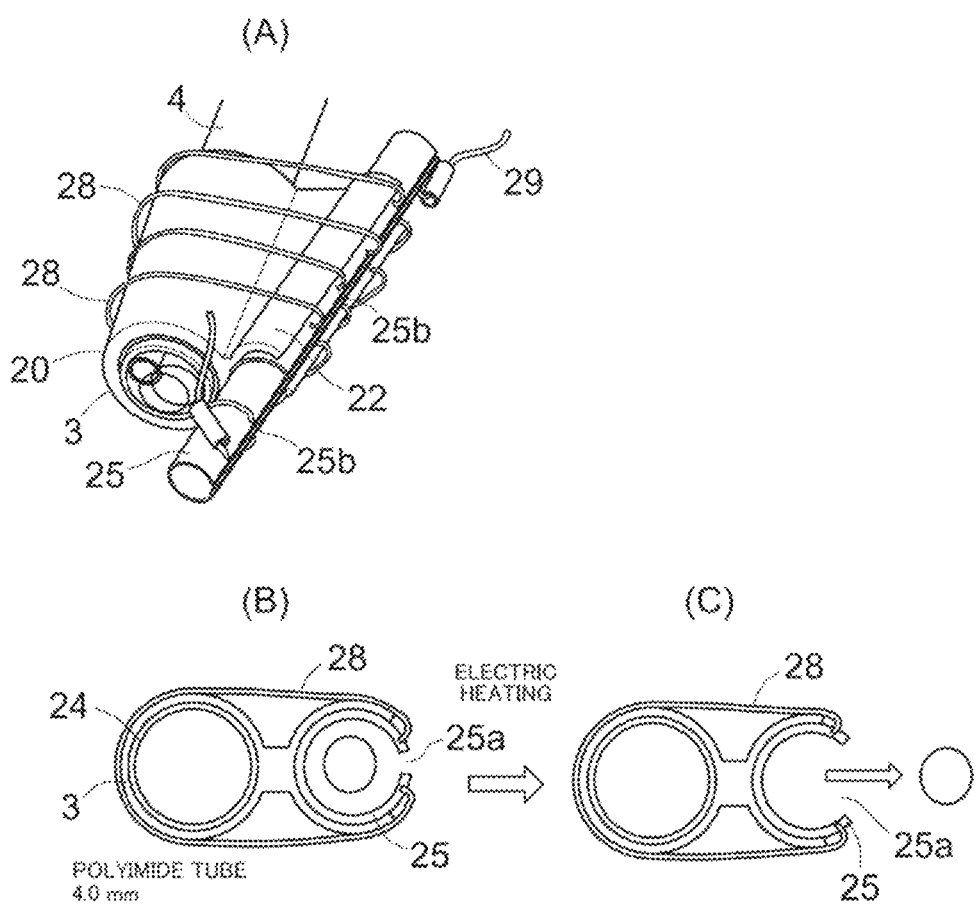
FIG. 8A illustrates an example of a shape-memory alloy wire type cochlear implant release mechanism.
FIG. 8B illustrates a state in which the cochlear implant is held.
FIG. 8C illustrates a state in which the cochlear implant is released.

Next, the angle θ (where θ is an acute angle greater than 0°) formed by the extending direction of the main body 20 (and the sheath 4 of the endoscope 2) and the extending direction of the holding portion 22 and the tubular member 25 of the cochlear implant insertion-assisting device 3 will be described with reference to FIG. 5. When the linear portion of the tip that includes the electrode portion 52 of the cochlear implant 50 is inserted into the cochlea, the tip portion of the tubular member 25 is preferably observed with the endoscope 2. Accordingly, the tubular member 25 is inclined with respect to the sheath 4 of the endoscope 2. A hole is opened in the retrotympanum 60 of the patient, and the linear portion of the tip including the electrode portion 52 of the cochlear implant 50 is passed through the cochlea fenestration 62 through the hole. The size of the retrotympanum 60 is approximately 3 mm×6 mm in diameter, and the size of the hole opened in the retrotympanum 60 is approximately 1.2 mm in diameter. To observe how the cochlear implant 50 is advancing, the tip of the sheath 4 of the endoscope 2 is brought as close as possible to the cochlea fenestration 62. Based on the relationship between the size of the tissue illustrated in the drawings and the size of the cochlear implant insertion-assisting device 3, it is preferable that the angle θ be approximately 30°.

Next, a method of using the cochlear implant insertion-assisting device 3 will be described with reference to FIG. 6A and FIG. 6B. As illustrated in FIG. 6A, in the case of inserting and installing the cochlear implant 50 into the cochlea, an operator such as a doctor or a researcher first pulls up the cochlear implant insertion-assisting device 3 attached to the sheath 4 of the endoscope 2 to the proximal side of the sheath 4, and brings the tip portion of the sheath 4 close to the retrotympanum 60. Next, the operator brings a drill 26 close to the retrotympanum 60 with the hand opposite to the hand holding the endoscope 2, drills a hole for inserting the cochlear implant 50, and retrieves the drill 26 when this operation is completed. Next, as illustrated in FIG. 6B, while holding the endoscope 2, the operator moves the cochlear implant insertion-assisting device 3 along the sheath 4 to the tip of the sheath 4 with the hand opposite to the hand holding the endoscope 2. Next, the cochlear implant 50 is passed through the holding portion 22 of the cochlear implant insertion-assisting device 3 with the hand opposite to the hand holding the endoscope 2, the tip portion including the electrode portion of the cochlear implant 50 is set in the cochlea fenestration 62 through the hole opened in FIG. 6A with the holding portion 22. The series of operations in FIG. 6A and FIG. 6B can be observed with the endoscope 2 while the operator holds the endoscope with one hand.

The cochlear implant insertion-assisting device 3 further includes a cochlear implant release mechanism for releasing the cochlear implant 50 from the holding portion 22.

An example of such a cochlear implant release mechanism is illustrated in FIG. 7A to FIG. 7D. As illustrated in FIG. 7A and FIG. 7C, a tubular member 25 that serves as a first tubular member is inserted into the holding portion 22 of a rotary detachable cochlear implant insertion-assisting device 3. The tubular member 25 includes a cut 25a that extends in the longitudinal direction. In addition, a second tubular member 27 is provided inside the tubular member 25. The second tubular member 27 includes a cut 27a that extends in the longitudinal direction and is configured to be movable in the circumferential direction in the tubular member 25. The tubular members 25 and 27 may also be famed from any material, but are preferably famed from a synthetic resin such as polyolefin or polyimide. The width of the cuts 25a and 27a is greater than the diameter of the cochlear implant 50. The tubular member 25 and the second tubular member 27 constitute the cochlear implant release mechanism. That is, from the states illustrated in FIG. 7A and FIG. 7C, an operator grips the second tubular member 27 with a hand or a gripping tool such as a forceps, and moves the second tubular member 27 in the circumferential direction within the tubular member 25. In the states illustrated in FIG. 7B and FIG. 7D, that is, when the operator sets the tubular member 27 to a state where the cut 27a of the second tubular member 27 is positioned in the cut 25a of the tubular member 25 such that the cuts 25a and 27a are aligned, the cochlear implant 50 detaches from the cochlear implant insertion-assisting device 3. In this way, the cochlear implant insertion-assisting device 3 can selectively switch between a first state in which the cochlear implant 50 is held and a second state in which the cochlear implant 50 can be released.

Another example of the cochlear implant release mechanism is illustrated in FIG. 8A to FIG. 8C. As illustrated in FIG. 8A, on the main body 20, the connection portion 21, and the holding portion 22 of the shape-memory alloy wire type cochlear implant insertion-assisting device 3, one or a plurality (one in the drawing) of shape-memory alloy wires 28 (also referred to as Shape Memory Alloy (SMA) wires) are wound along the longitudinal direction of the main body 20 (the longitudinal direction of the sheath 4 of the endoscope 2) in a meandering manner in a direction that is substantially perpendicular (left and right in the drawing) to the longitudinal direction of the main body 20. A plurality of holes 25b are provided in two opposing end portions that define the cut 25a of the tubular member 25, and the corresponding shape-memory alloy wire 28 is attached thereto. In the present embodiment, the configuration of the shape-memory alloy wire 28 illustrated in FIG. 8A is formed by repeating a process in which the shape-memory alloy wire 28 is wound around the main body 20, inserted into the hole 25b at one end of the tubular member 25, and drawn out from the hole 25b adjacent to this hole 25b, the shape-memory alloy wire 28 is wound around the main body 20 while separating from the aforementioned winding portion around the main body 20 in the longitudinal direction of the main body 20, inserted into the hole 25b at the other end of the tubular member 25, and drawn out from the hole 25b adjacent to this hole 25b. The upper and lower portions of the shape-memory alloy wire 28 are connected to a copper wire 29. The tubular members 24 and 25 may also be formed from any material, but are preferably formed from a synthetic resin such as polyolefin or polyimide. In addition, the shape-memory alloy wire 28 may be covered with a synthetic resin tube (polymer tube) for the purpose of waterproofing and electrical insulation of the shape-memory alloy wire 28. The cochlear implant release mechanism is constituted by the tubular member 25 and the shape-memory alloy wire 28.

When the copper wire 29 is electrified from a power source (not illustrated) from the state illustrated in FIG. 8B, the space between both ends of one shape-memory alloy wire 28 is opened, and the width of the cut 25a of the tubular member 25 expands as illustrated in FIG. 8C. When the width of the cut 25a of the tubular member 25 becomes greater than the diameter of the cochlear implant 50, the cochlear implant 50 is removed from the cochlear implant insertion-assisting device 3. When not electrified, the shape-memory alloy wire 28 assists the holding of the object (cochlear implant 50) held by the holding portion 22 without allowing change in the width of the cut 25a. When electrified, the shape-memory alloy wire 28 expands the width of the cut 25a to assist releasing of the held object (cochlear implant 50). In this example as well, the cochlear implant insertion-assisting device 3 can selectively switch between a first state in which the cochlear implant 50 is held and a second state in which the cochlear implant 50 can be released.

The present invention has been described with reference to the first embodiment, but the present invention is not limited to this, and various modifications as described below are also possible.

The configuration for holding and releasing the cochlear implant 50 of the cochlear implant insertion-assisting device 3 can also be applied as an elongated medical instrument holding mechanism for holding and releasing elongated medical instruments other than the cochlear implant 50. Here, elongated means that the length dimension in the length direction is longer (for example, 10 times or more) than a dimension in the width direction perpendicular to the length direction. Elongated medical instruments include ear implants such as cochlear implants, middle ear implants, and artificial ear ossicles, fibers for laser irradiation, guide wires, surgical instruments such as forceps and raspatories, tubular insertion tools for Drug Delivery Systems (DDS), cord-shaped medical instruments that bend in a free state, and the like. Cord-shaped medical instruments that bend in a free state also include tubular insertion tools for cochlear implants, middle ear implants, and DDSs.

Figure 9:
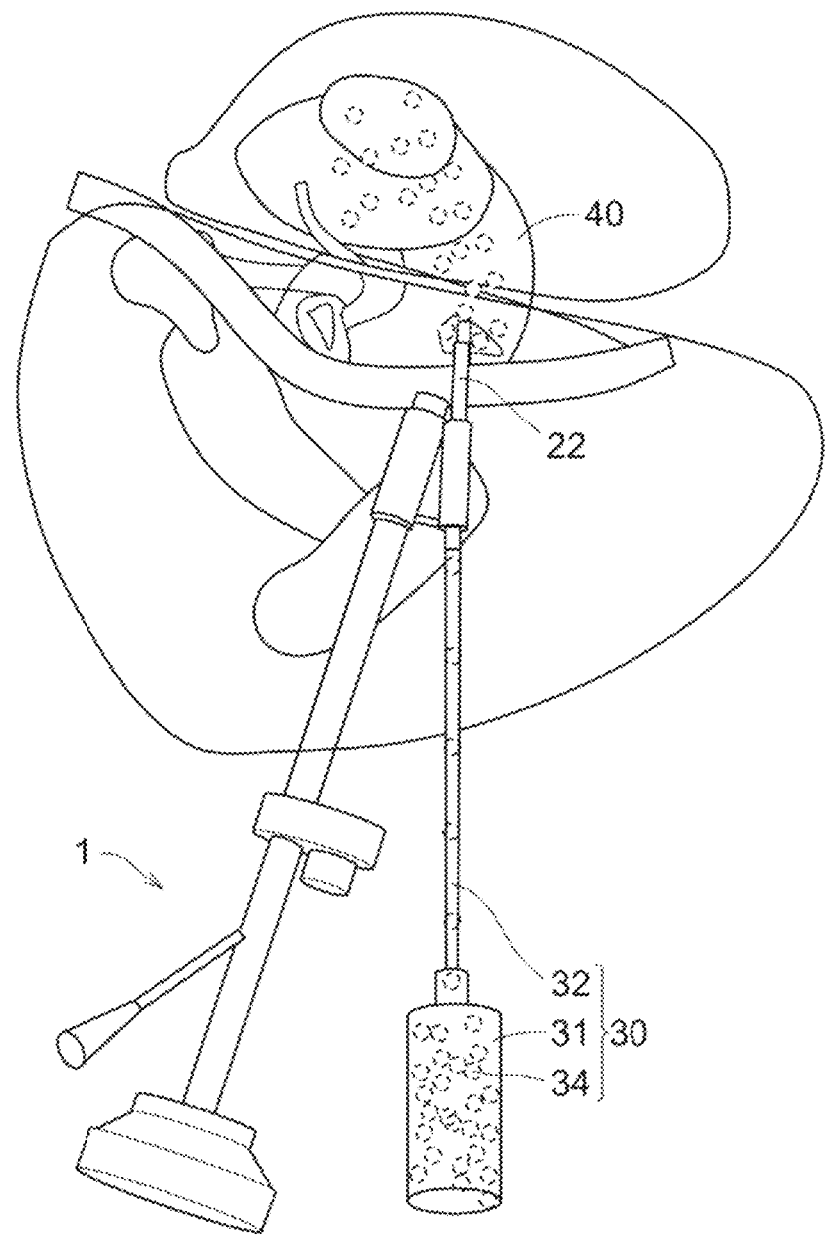
FIG. 9 illustrates an example of drug delivery using an underwater otological surgery endoscope provided with a holding mechanism for elongated medical instruments.

For example, FIG. 9 illustrates an example of drug delivery using an underwater otological surgery endoscope provided with a holding mechanism for elongated medical instruments. In the holding portion 22 of the holding mechanism of the elongated medical instrument illustrated as having the same configuration as the cochlear implant insertion-assisting device 3, the underwater otological surgery endoscope 1 holds an elongated pipe 32 of the tube 30 that serves as an elongated medical instrument. The tube 30 is a tubular insertion tool for a drug delivery system. By causing the tube 30 to approach or enter the inner ear 40 and delivering an injection substance 34 such as drugs, genes, or regeneration cells housed in the housing portion 31 of the tube 30 while the operator protects the inner ear 40 under perfusion, the injection substance 34 can be injected directly from the tip of the pipe 32 to the injection site through the tube 32 that communicates with the housing portion 31. The tube 30 may be indwelt only during surgery, or can be indwelt after surgery as well.

In addition, for example, in the case where the elongated medical instrument is an artificial ear ossicle, stapedotomy or stapedectomy is performed while protecting the inner ear by the underwater endoscope 2, the holding mechanism of the elongated medical instrument is used as a guiding device for the artificial ear ossicle, and the artificial ear ossicle is accurately inserted and set using gripping forceps or the like under the guidance of the sheath 4. Furthermore, in the case that the elongated medical instrument is a flex fiber for laser irradiation, the holding mechanism of the elongated medical instrument may be used as the guiding device of the flex fiber, the laser flex fiber may be inserted under the guidance of the sheath 4, and the flex fiber may be moved with the tip portion of the sheath 4 of the endoscope serving as a fulcrum in order to use the laser at a wider angle with greater accuracy. In this regard, holmium lasers and the like are used underwater, but with regard to $CO_2$ lasers and the like that are absorbed underwater, a suction device may be attached to the cap 17 illustrated in FIG. 1 to absorb the smoke generated from the liquid perfusion tube 15 during laser use. In this case, the operability of the flex fiber is improved, the field of view resulting from perfusion is secured, and excessive temperature increase can also be suppressed.

A pipe for drug delivery may be further provided inside the sheath 4 of the endoscope 2 illustrated in FIG. 3. Alternatively, drugs may be mixed into the perfusion fluid and poured into the perfusion tube 15. In any case, the inner ear (cochlea, vestibule, semicircular canal) is fenestrated with the use of the underwater endoscope 2 of the present invention, the tubular member 25 is brought close to or inserted into the fenestrated portion under the guide of the sheath 4, and drugs or the like are injected. In this way, as a DDS for inner ear disease, it is possible to efficiently administer drugs, gene therapy, or regenerative medicine (such as cells) locally while protecting the inner ear tissue under perfusion.

The hole 16 provided in the sheath 4 and the liquid perfusion tube 15 illustrated in FIG. 1 to FIG. 3, which are liquid perfusions systems, may be omitted or may have other configurations.

The cochlear implant insertion-assisting device 3 of FIG. 4 is provided with a main body 20 attached around the sheath 4 of the endoscope 2, the connection portion 21, and the holding portion 22 configured to hold the connection portion 21 and the cochlear implant 50, but the connection portion 21 may be omitted. Provided that the cochlear implant insertion-assisting device 3 is provided with a portion for attachment to the sheath of the endoscope and a holding portion configured to hold the cochlear implant 50, other configurations are also possible.

The disclosures of all patent applications and literature cited herein are hereby incorporated by reference in their entirety.

Hereinafter, the present invention will be described in detail with reference to examples, but the present invention is not limited thereto.

EXAMPLES

Example 1

Manufacture of an Ear Endoscope System

The underwater otological surgery endoscope 2 illustrated in FIG. 10A and FIG. 10B was manufactured. A stainless steel pipe SUS304 having an outer diameter of 3.75 mm and an inner diameter of 3.19 mm was used for the sheath 4 of the endoscope 2. A rod lens (GRINTECH, GT-ERLS-200-175-0005-P9) having a φ of 2.0 mm and a length of 184 mm was used for the rod lens 5. To guide the illumination light from the light source device to the tip portion of the endoscope 2, a bundle of optical fibers 13 having a φ of 155 μm (FURUKAWA ELECTRIC CO., LTD, F68519) was disposed inside the endoscope as an illumination system. A tube made of silicone rubber and having an outer diameter of 1.3 mm and an inner diameter of 1.0 mm was used as the liquid perfusion tube 15. The total length of the endoscope 2 was 195 mm.

Figure 11:
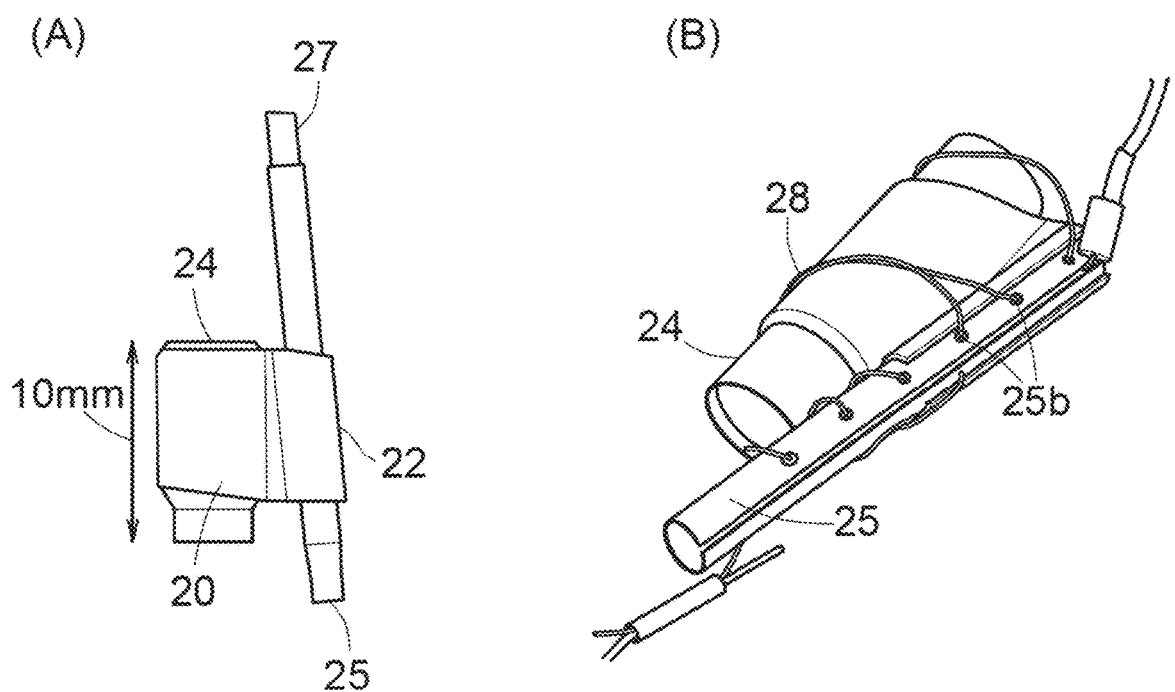
FIG. 11A illustrates an example of the formation of a device having a rotation-type cochlear implant release mechanism.
FIG. 11B illustrates an example of the formation of a device having a shape-memory alloy wire type cochlear implant release mechanism.

Next, a urethane gel sheet (EXSEAL Co., Ltd, hardness of 15 degrees) and a polyimide tube (FURUKAWA ELECTRIC CO., LTD, PIT-S) were bonded with an elastic adhesive to manufacture a device having a rotation-type cochlear implant release mechanism as illustrated in FIG. 11A. A polyimide tube having an outer diameter of 4.0 mm was used as the tubular member 24. A polyimide tube having an outer diameter of 1.8 mm was used as the tubular member 25. A polyimide tube having an outer diameter of 1.5 mm was used as the second tubular member 27. The angle θ formed between the holding portion 22 and the extending direction of the tubular member 25 was set to 17°.

In the case of manufacturing a device having a shape-memory alloy wire type cochlear implant release mechanism as illustrated in FIG. 11B, a hole 25b is famed in the tubular member 25, which is a polyimide tube having an outer diameter of 4.0 mm, with a Nd-YAG laser. Then, an SMA wire 28 having a φ of 100 μm (TOKI Corporation, BMF 100) was passed through the hole 25b and wound. The tubular member 24 and the tubular member 25 were fixed with a urethane gel sheet.

Example 2

Figure 12:
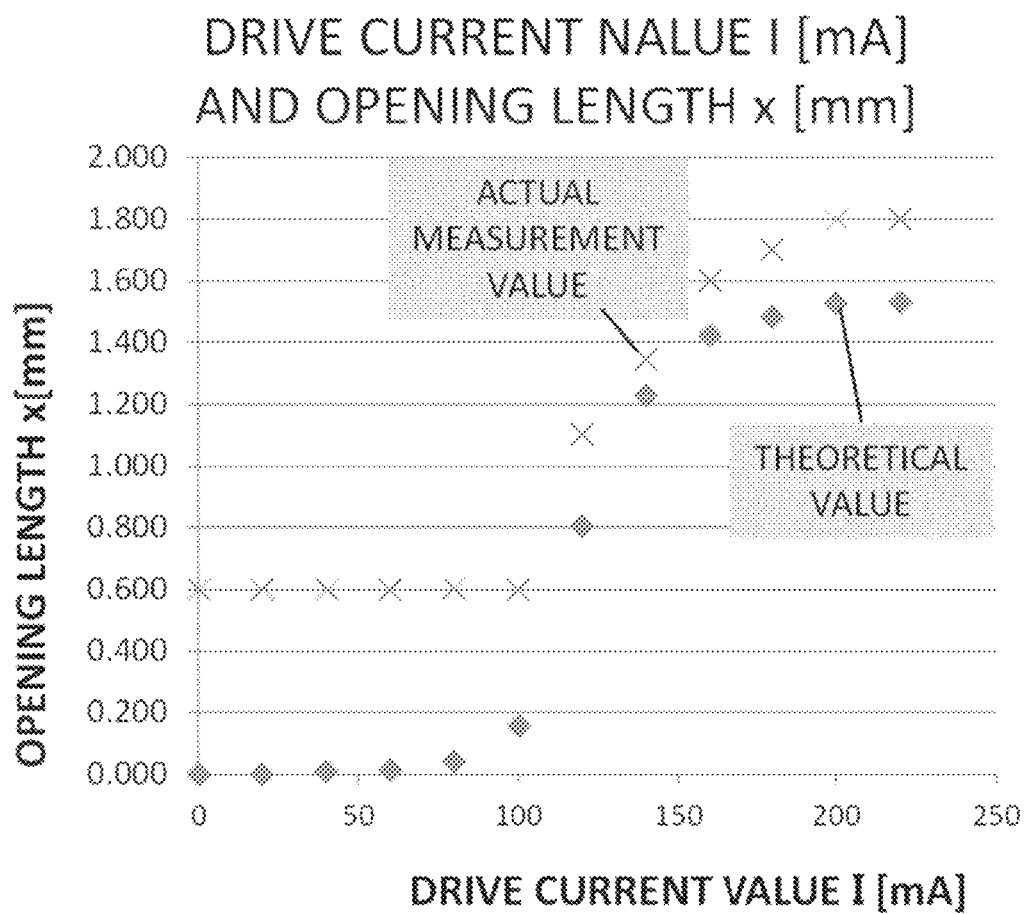
FIG. 12 is a graph illustrating a relationship between a driving current value and an opening length.

Operation Verification of Shape-Memory Alloy Wire Type (SMA Type) Cochlear Implant Release Mechanism Drive current was passed through a device having a shape-memory alloy wire type cochlear implant release mechanism as illustrated in FIG. 11B, and the width of the cut 25a (opening length) of the tubular member 25 was measured for different current values. As a result, as illustrated in FIG. 12, an opening length of approximately 0.6 mm was obtained with a driving current of from 0 to 100 mA, and an opening length of 1.8 mm was confirmed when a driving current of 200 mA was passed.

Example 3

Evaluation Experiment for Perfusion System

Figure 13:
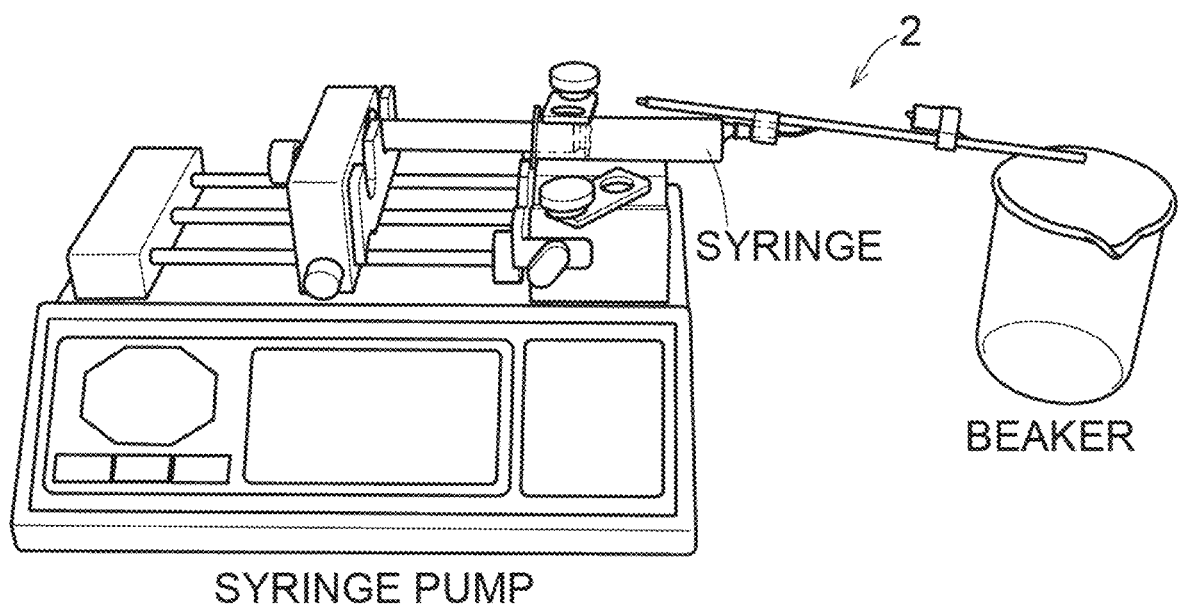
FIG. 13 is a schematic diagram of an experimental device of a perfusion system.

Using a syringe pump, the flow rate of perfusion fluid was defined to be 1167 μm/min≈70 ml/h, which is the required specification. Perfusion fluid inserted into a syringe with a volume of 10 ml was poured through a silicone rubber tube having an outer diameter of 1.3 mm and an inner diameter of 1.0 mm into an empty beaker for 1 minute (FIG. 13). Subsequently, the weight of the beaker was measured, and the amount of water that actually flowed was verified.

As a result, although there is a measurement error due to the trace amount of perfusion fluid droplets that remain in the silicone rubber tube, it was verified that the perfusion system of the underwater otological surgery endoscope produced in the present example can satisfy the required flow rate specification of 70 ml/h.

Example 4

Figure 14:
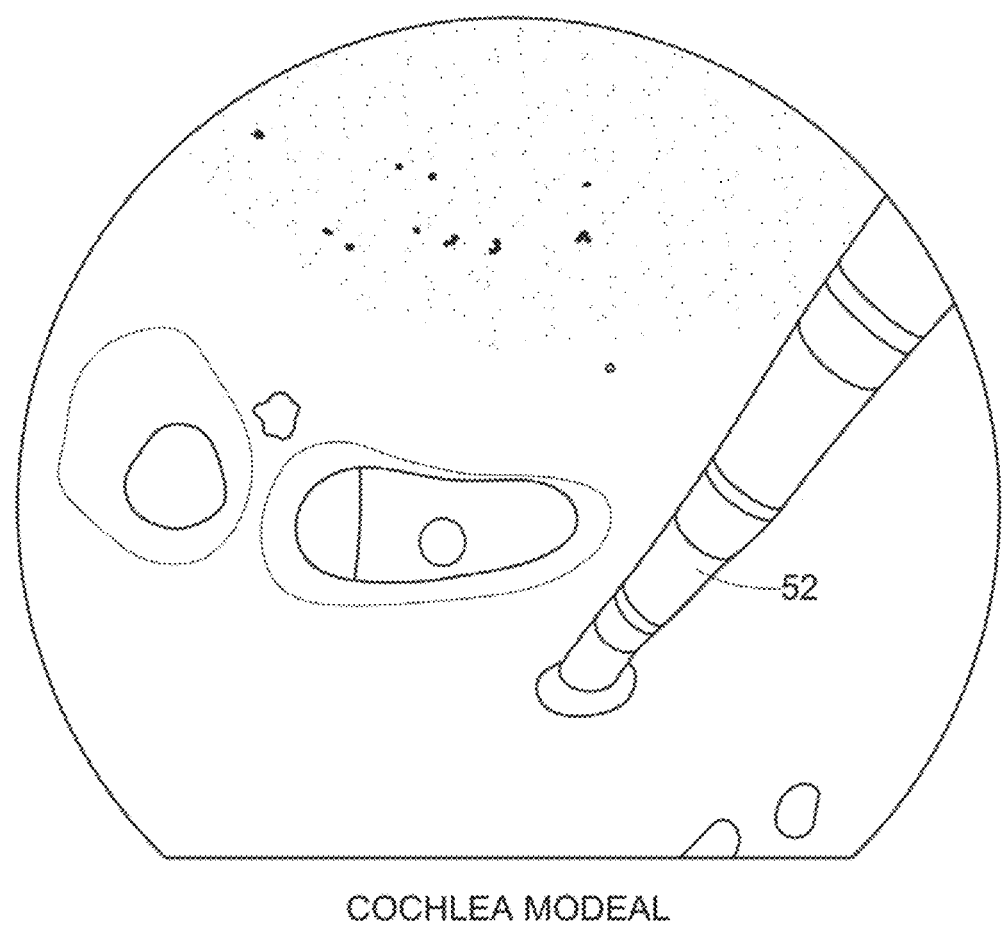
FIG. 14 is a photograph of a cochlea model.

Evaluation Experiment of Cochlear Implant Insertion Assistance Using Cochlea Model To verify whether or not it is possible to obtain a satisfactory field of view by observation with the underwater otological surgery endoscope produced in Example 1, and whether or not it is possible to smoothly perform surgery using the produced CI insertion assistance mechanism, a model surgery similar to an actual cochlear implant surgery was performed in which a CI was inserted into the cochlea insertion hole of an inner ear using a cochlea model. In this regard, the guiding time and the insertion time were compared between an insertion method using an otological surgery endoscope equipped with a CI insertion assistance mechanism and a CI insertion method using gripping forceps for cochlear implant insertion in which the CI insertion assistance mechanism was not used. FIG. 14 illustrates how the CI is inserted by the gripping forceps for cochlear implant insertion. The cochlea model used in the present experiment was the Cochlear Right TB-Round Window Electrode Insertion Model Z256138.

Experimental Method

The CI insertion assistance mechanism was evaluated in the following three situations by conducting model surgery.
(A) A case where only forceps are used (the current CI insertion technique)
(B) A case where a CI insertion-assisting device having a rotary type CI release mechanism was used
(C) A case where a CI insertion-assisting device with an SMA type CI release mechanism was used In this regard, three sets of two points, t1: the time until the CI tip is inserted into the cochlea fenestration, and t2: the time until the CI is deeply inserted (the time from the insertion of the first electrode to the insertion of the seventh electrode), were measured, and the average time of each was determined.

The results are showed in Table 1. By using the CI insertion-assisting device, as the tip of the tubular member 25 of the CI insertion-assisting device can be brought close to the insertion portion of the cochlea, in addition to improvement in the guidance of the CI, insertion of the CI is also improved since force is applied straight in the insertion direction to the cochlea without bending of the CI. For this reason, in (B) and (C) in which the CI insertion-assisting device was utilized, the time taken to install the CI was greatly shortened in comparison with the current CI insertion technique (A).

TABLE 1

Evaluation Test Results

|  | (A) Forceps only | (B) Rotary Detachable Type | (C) SMA Type |
|---|---|---|---|
| t1: Time when first electrode is inserted | 200 seconds | 28 seconds | 52 seconds |
| t2: Average time value when electrodes 1 to 7 are inserted | 62 seconds | 19 seconds | 22 seconds |

Example 5

Investigation of Influence of Perfusion on Temperature Change of Cochlea Model

A rigid endoscope (1218A 0° 4 mm diameter, Karl Storz, Germany) was fixed to the same temporal bone model (cochlea model) as in Example 4, and a sensor of a thermometer (Model BAT-12, Physitemp Instruments Inc., United States of America) was fixed at a position with a distance 3 mm away from the endoscope. The temperature was measured every 1 minute for 15 minutes after turning on the light source (Xenon nova, Karl Storz, Germany), and after 15 minutes the light was extinguished and measurement was further continued for an additional five minutes. The temperature measurements were carried out under a condition in which there was no perfusion in the endoscope ((A) in FIG. 15), and under a condition in which perfusion was initiated at the same time as the light source was turned on ((B) in FIG. 15). With regard to the perfusion, perfusion fluid was introduced from the side of the endoscope through a 0.4 mm polyamide tube with a perfusion pump (13-876-2 Model 3386, Ficher Scientific Control Company), and the tip of the endoscope was immersed to establish an underwater endoscope condition.

Figure 15:
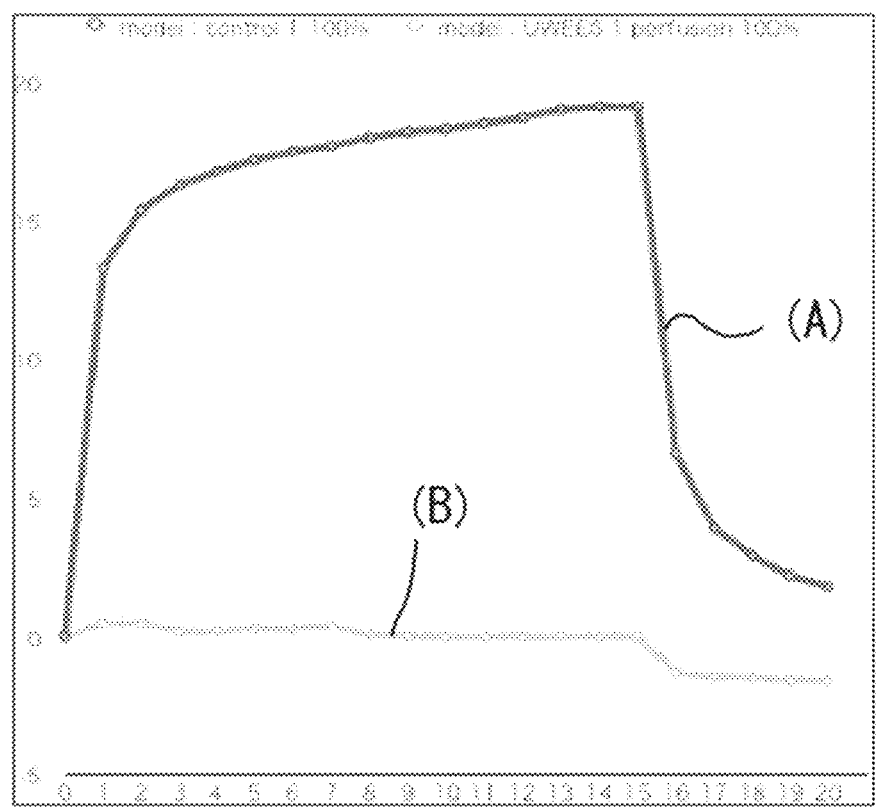
FIG. 15 is a graph illustrating a temperature change in a temporal bone model. (A) in FIG. 15 illustrates a case of using an endoscope under normal conditions without perfusion, and (B) in FIG. 15 illustrates a case of using an endoscope with perfusion (6 ml/ml) conditions (underwater otological surgery).
Figure 16:
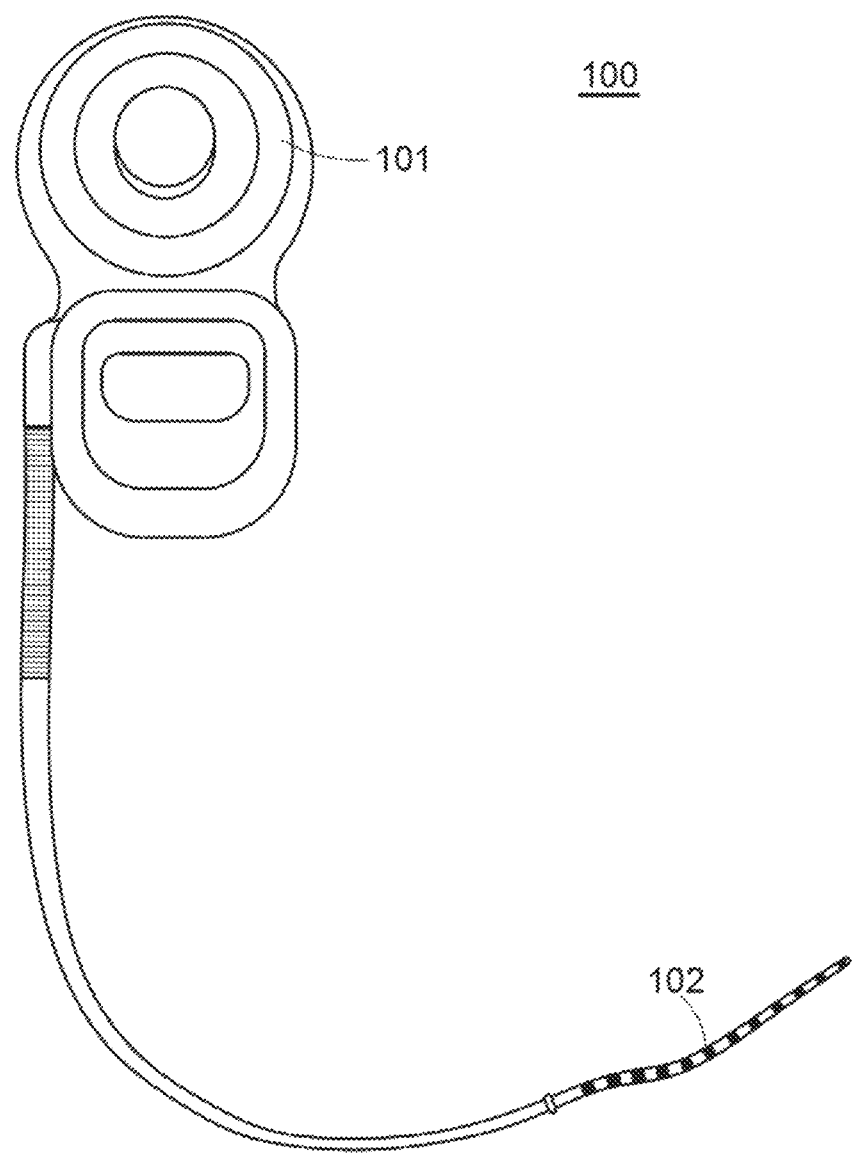
FIG. 16 illustrates an example of an intra-corporeal device of a cochlear implant (CI).
Figure 17:
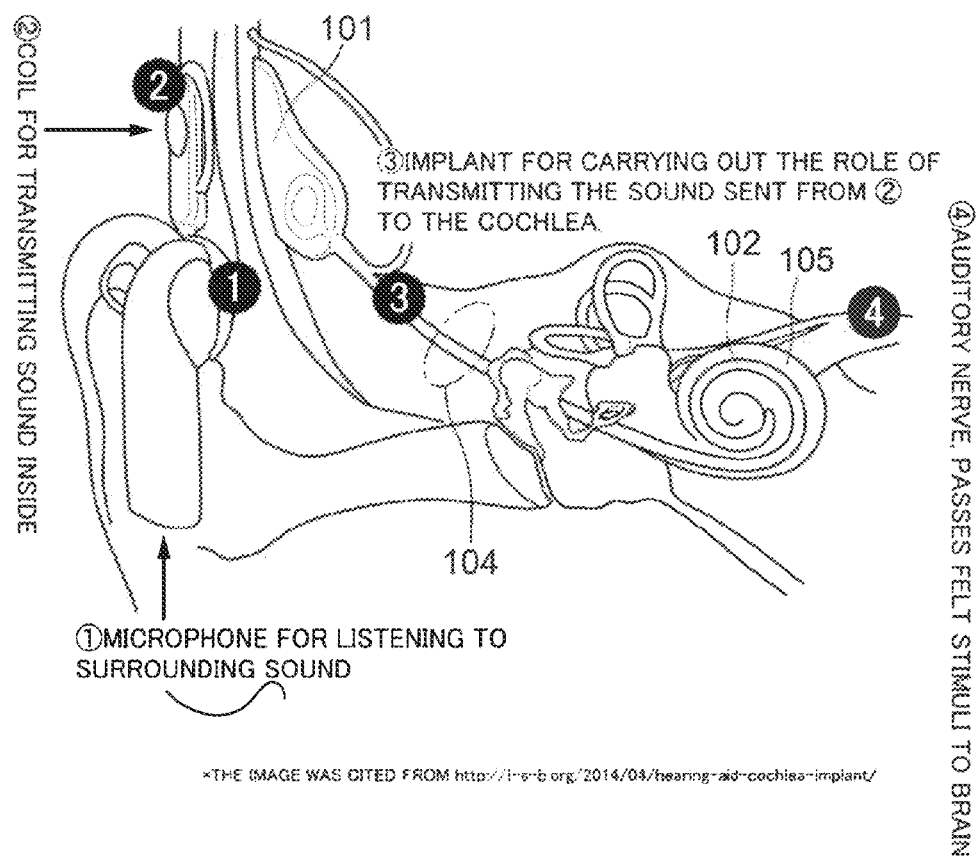
FIG. 17 is a diagram for illustrating implanting of an intra-corporeal device of a cochlear implant in an inner ear.

As illustrated in (A) in FIG. 15, although a temperature increase due to the light source occurs when the endoscope is brought close to the temporal bone model, as illustrated in (B) in FIG. 15, in underwater endoscopes, this temperature increase can be prevented by perfusion. This result indicates that perfusion can prevent tissue injury due to burns. Although embodiments and examples of the present invention have been described in detail above, the present invention is not limited to the above-described embodiments, and various modifications based on the technical ideas of the present invention are possible.

The present invention can also utilize the following configurations.

(1) A holding mechanism for a medical instrument having an elongated shape, the holding mechanism including:
a tubular member configured to hold a medical instrument; wherein the tubular member includes a cut extending in a longitudinal direction, and
the holding mechanism can selectively switch between a first state in which the medical instrument is held and a second state in which the medical instrument can be released.

(2) The holding mechanism according to (1), wherein the tubular member includes:
a first tubular member including a cut extending in a longitudinal direction, and
a second tubular member including a cut extending in the longitudinal direction and disposed inside the first tubular member,
widths of the first tubular member and the second tubular member are greater than a diameter of the medical instrument; and in the second state, a position of the cut of the first tubular member and a position of the cut of the second tubular member are aligned by rotating the second tubular member, and the medical instrument held inside the second tubular member is allowed to be released.

(3) The holding mechanism according to (1), wherein in the second state, the tubular member allows the medical instrument held inside to be released by expanding a width of the cut to be greater than an outer diameter of the medical instrument.

(4) The holding mechanism according to (3), wherein
a shape-memory alloy wire is wound around the tubular member; and
in the second state, the width of the cut of the tubular member expands to be greater than an outer diameter of the medical instrument by shrinking of the shape-memory alloy wire due to electric heating, and the medical instrument is allowed to be released.

(5) The holding mechanism according to (4), wherein a polymer tube covers the shape-memory alloy wire.

(6) The holding mechanism according to any one of (1) to (5) wherein the medical instrument is an ear implant or a fiber for laser irradiation.

(7) The holding mechanism according to any one of (1) to (5) wherein the medical instrument is a cochlear implant or an artificial ear ossicle.

(8) The holding mechanism according to any one of (1) to (7) wherein the holding mechanism is an attachment device configured to be attached to an endoscope.

(9) An endoscope system including: an endoscope including a sheath; and
the holding mechanism according to any one of (1) to (7) mounted to be movable along the sheath.

(10) An endoscope system including:
the holding mechanism according to (9), which is an ear endoscope system.

(11) The ear endoscope system according to (9) or (10), wherein a liquid perfusion pipe is provided inside the sheath of the endoscope.

(12) The ear endoscope system according to any one of (9) to (11), wherein a drug delivery pipe is provided inside the sheath of the endoscope.

(13) An attachment device configured to be attached to an endoscope including a sheath, the attachment device including:
a hollow main body configured to be attached around a sheath of an endoscope; and a tubular member connected to the main body and configured to hold an elongated medical instrument.

(14) The attachment device according to (13), wherein the tubular member includes:
a first tubular member including a cut extending in a longitudinal direction, and
a second tubular member including a cut extending in the longitudinal direction and disposed inside the first tubular member,
widths of the first tubular member and the second tubular member are greater than a diameter of the medical instrument; and
in the second state, a position of the cut of the first tubular member and a position of the cut of the second tubular member are aligned by rotating the second tubular member, and the medical instrument held inside the second tubular member is allowed to be released.

(15) The attachment device according to (13), wherein in the second state, the tubular member allows the medical instrument held inside to be released by expanding a width of the cut to be greater than an outer diameter of the medical instrument.

(16) The attachment device according to (15), wherein a shape-memory alloy wire is wound around the tubular member; and in the second state, the width of the cut of the tubular member expands to be greater than an outer diameter of a medical instrument by shrinking of a shape-memory alloy wire due to electric heating, and a medical instrument is allowed to be released.

(17) The attachment device according to (16), wherein a polymer tube covers a shape-memory alloy wire.

(18) The attachment device according to any one of (13) to (17), wherein the medical instrument is an ear implant or a fiber for laser irradiation.

(19) The attachment device according to any one of (13) to (17), wherein the medical instrument is a cochlear implant or an artificial ear ossicle.

(20) An endoscope system including: an endoscope including a sheath; and
the attachment device according to any one of (1) to (19) mounted to be movable along the sheath.

INDUSTRIAL APPLICABILITY

The elongated medical instrument holding mechanism of the present invention is useful in that the guiding and releasing of a medical instrument to a predetermined position can be easily and quickly performed. For example, when the present invention is applied to a cochlear implant insertion-assisting device, it is useful in that the labor and time for insertion of a cochlear implant can be reduced.

The invention claimed is:

1. A holding mechanism for a medical instrument having an elongated shape, the holding mechanism comprising:
a main body that is hollow and has a cylindrical shape;
a holding portion connected in parallel to the main body and including an opening along an entire length of the holding portion in a longitudinal direction; and
a tubular member inserted in the holding portion and configured to hold the medical instrument provided in the holding portion, wherein
the tubular member includes a cut extending an entire length of the tubular member in the longitudinal direction,
the tubular member has a length longer than that of the holding portion, and
the holding mechanism can selectively switch between a first state in which the medical instrument is held and a second state in which the medical instrument can be released through the cut in the tubular member.

2. The holding mechanism according to claim 1, wherein the tubular member is a first tubular member,
wherein the holding mechanism further comprises a second tubular member including a cut extending an entire length of the second tubular member in the longitudinal direction, the second tubular member being disposed inside the first tubular member,
a width of the cut of the first tubular member and a width of the cut of the second tubular member are greater than a diameter of the medical instrument, and
in the second state, a position of the cut of the first tubular member and a position of the cut of the second tubular member are aligned by rotating the second tubular member, and the medical instrument held inside the second tubular member is allowed to be released.

3. The holding mechanism according to claim 1, wherein, in the second state, the tubular member allows the medical instrument held inside to be released by expanding a width of the cut to be greater than an outer diameter of the medical instrument.

4. The holding mechanism according to claim 3, wherein a shape-memory alloy wire is wound around the tubular member, and
in the second state, the width of the cut of the tubular member expands to be greater than the outer diameter of the medical instrument by shrinking of the shape-memory alloy wire due to electric heating, and the medical instrument is allowed to be released.

5. The holding mechanism according to claim 4, wherein a polymer tube covers the shape-memory alloy wire.

6. The holding mechanism according to 1, wherein the medical instrument is a cochlear implant or an artificial ear ossicle.

7. The holding mechanism according to claim 1, wherein the holding mechanism is an attachment device configured to be attached to an endoscope.

* * * * *